United States Patent [19]

Lindquist et al.

[11] 4,086,222
[45] Apr. 25, 1978

[54] METHOD OF ISOLATING ALBUMIN FROM BLOOD PRODUCTS

[75] Inventors: Lars-Olof Edvard Lindquist; Jan Hakan Berglof; John Malcolm Curling, all of Uppsala, Sweden

[73] Assignee: Pharmacia Fine Chemicals AB, Uppsala, Sweden

[21] Appl. No.: 727,611

[22] Filed: Sep. 28, 1976

[30] Foreign Application Priority Data

Oct. 9, 1975 Sweden .............................. 75112953

[51] Int. Cl.$^2$ ...................... B01D 15/08; A2D 1/00
[52] U.S. Cl. ...................... 260/122; 210/DIG. 23; 210/31 C
[58] Field of Search ......... 210/31 C, 198 C, DIG. 23; 55/67, 386; 23/230 B; 260/122

[56] References Cited

U.S. PATENT DOCUMENTS

| 3,657,116 | 4/1972 | Haller | 210/31 C |
| 3,959,128 | 5/1976 | Harris | 210/DIG. 23 |

OTHER PUBLICATIONS

Separation of Neutral Proteins on Ion-Exchange Resins by Boardman et al. in Biochemical Journal, vol. 59, No. 4, Apr. 1955, pp. 543, 552.

*Primary Examiner*—John Adee
*Attorney, Agent, or Firm*—Bacon & Thomas

[57] ABSTRACT

This invention relates to a new method of isolating highly purified albumin in high yields from plasma products.

According to the invention a particular plasma fraction, containing albumin in dissolved form and being essentially free from the coagulation factors I, II, VII, VIII, IX and X and from the main part of IgG, is subjected to a two-step chromatographic separation using aqueous buffer systems. The first step is carried out on an anion exchanger and the second step on a cation exchanger, or vice versa. In a preferred embodiment a buffer of pH 4.5 – 4.9 and an ionic strength of 0.025 – 0.1 is used for the separation on the anion exchanger, whereas a buffer of pH 5.2 – 6.5 and an ionic strength of 0.1 – 0.05 is used for the separation on the cation exchanger.

5 Claims, No Drawings

METHOD OF ISOLATING ALBUMIN FROM BLOOD PRODUCTS

The invention relates to a new method of isolating albumin from blood products.

Previously known methods for the isolation of plasma proteins from blood products are almost exclusively based on the Cohn fractionation method using cold ethanol, which was developed already in the 1940-ies (see e.g. Cohn et al., J. Am. Chem. Soc. 68 (1946), 459-475). In spite of the extensive use of this method, it has several drawbacks and limitations. For example, the use of ethanol contributes to denaturation and inactivation of many valuable, biologically active plasma proteins. Furthermore, the method is complex and time consuming as it comprises many steps of treatment and only can be carried out batch-wise. When using the Cohn method for isolating albumin, which is mainly used as a plasma expander/substitute, the yield only amounts to about 55 - 60% (Proc. Roy. Soc. Edinburgh (B) 71 (Suppl.) 1972, p. 31).

The demand of highly purified albumin is greater than the supply and there is an urgent need for new and improved methods for isolating albumin from plasma products. It is in this connection especially important to increase the yield, as the supply of the raw material is limited.

The present invention, which aims at meeting this need, relates to a new method of isolating albumin, which offers considerably higher total yields — of the order of 90% or more — than the previously known fractionation methods, the albumin product obtained having at least the same degree of purity as the products obtained by means of the known fractionation methods. The new method requires only few steps of treatment, and no protein destructing solvents such as ethanol, but only aqueous solutions are used. Furthermore, the new method can preferably be designed as a continuous and automatized process.

The method according to the invention is based on a two-step chromatographic ion exchange separation of a specific plasma fraction, which is essentially free from the coagulation factors I, II, VII, VIII, IX and X and also from the main part of IgG. Such plasma fractions can be prepared in a manner known per se from human and non-human blood products such as blood plasma, blood serum, placental blood serum or placental extract, the coagulation factors in question being eliminated by means of conventional methods such as cryoprecipitation (factors I and VIII; see e.g. Pool, J.G. Thromb, Diath. Haemorrhag, Suppl. 35 (1967), 35-40) and adsorption on, for example, anion exchange polymers (factors II, VII, IX and X; see e.g. Heystek J. et al., Vox Sang. 25 (1973), 113-123 and do. 29 (1975), 177-183). The main part of IgG (together with, among other things, lipoproteins, macroglobulines and remaining fibrinogen) is preferably eliminated by precipitation with, for example, polyethylene glycol (PEG) — see e.g. Polson, A. et al., Vox Sang. 23 (1972), 107-118. The precipitate from said precipitation — i.e. the albumin poor fraction — may be collected for recovery of IgG and other plasma proteins, whereas the albumin rich fraction is used as the starting material in the method according to the invention. It should be underlined that the invention is not limited to the use of plasma starting materials, which have been prepared in any particular way, but any plasma fraction, which meets the above indicated requirements, can be used, e.g. also the fractions V, IV + V or IV of the Cohn process.

In the method according to the invention the pH of the starting material defined above is adjusted to about 5 - 7.5, preferably 6.5 - 7. This albumin solution is then subjected to two different chromatographic separations by means of ion exchangers, viz. one separation on an anion exchanger and the other on a cation exchanger. The two ion exchange separations may be carried out in arbitrary sequence, but it is preferred to start with the separation on the anion exchanger and then proceed with the separation on the cation exchanger. Aqueous buffer systems are used in the two chromatographic separation steps, a buffer of pH 4.5 - 4.9 and an ionic strength of 0.025 - 0.1 being used for the separation on the anion exchanger and a buffer of pH 5.2 - 6.5 and an ionic strength of 0.1 - 0.05 being used for the separation on the cation exchanger. Both separations are preferably carried out as conventional column chromatographic operations, but one or both of the steps may, as a principle, also be carried out batch-wise, i.e. by stirring a suspension of the ion exchanger, the albumin containing starting material and the buffer in question, although this procedure is less suitable from a practical viewpoint. Under the conditions indicated above contaminations, but not the albumin, are adsorbed on the ion exchanger. Thus, in each of the two separation steps the albumin is present in the eluate (when using ion exchange columns) or in the filtrate after the ion exchanger has been filtered off (when working batch-wise). The yield of albumin over the two chromatographic ion exchange separation steps is practically quantitative (in general > 99%) and the albumin solution obtained is very pure (more than 96%).

In the embodiment where the first separation step is carried out on an anion exchanger and the second separation step on a cation exchanger, it is preferred to start the separation on the anion exchanger with an introductory washing step using a buffer of pH about 5 - 5.5 and an ionic strength of about 0.025 - 0.1, thereby eliminating, among other things, possibly present haemoglobin and remaining IgG in the eluate, which is discarded or, if desired, treater further for the isolation of e.g. said components. The albumin is then eluted out by means of the above indicated buffer of pH 4.5 - 4.9 and an ionic strength of 0.025 - 0.1. The albumin rich eluate is collected for subsequent treatment on the cation exchanger.

The albumin rich eluate from the treatment of the anion exchanger is adjusted to pH 5.2 - 6.5, preferably 5.2 - 5.7, and an ionic strength of 0.1 - 0.05 and is then eluted out on the cation exchanger by means of a buffer of the same pH and the same ionic strength. The eluate obtained, which contains highly purified albumin, is then worked up in a manner known per se.

As mentioned above the two ion exchange separation steps may be carried out in reversed sequence, i.e. by first treating the starting fraction, as defined above, on the cation exchanger, and then treating the albumin rich fractions obtained in this separation on the anion exchanger. Also in this case the albumin fraction is eluted on the cation exchanger by means of an aqueous buffer of pH 5.2 - 6.5, preferably 5.2 - 5.7, and an ionic strength of 0.1 - 0.05, but in this embodiment it is not necessary, in the subsequent treatment on the anion exchanger, to carry out an introductory washing step at pH 5 - 5.5 and an ionic strength of 0.025 - 0.1, but it is possible to elute the albumin directly with a buffer of pH 4.5 – 4.9 and an ionic strength of 0.025 – 0.1, the eluate containing highly purified albumin which is ready for working-up.

After the ion exchangers have been used in the method according to the invention they are preferably regenerated for re-use in the process. The regeneration is carried out in a manner known per se, preferably by washing with the same type of buffer system as the one used for the separation treatments according to the invention. The eluates from the regenerating washing step contain some blood components which may, if desired, be isolated.

The albumin rich fraction obtained from the two-step chromatographic separation on the anion exchanger and on the cation exchanger (which, for example, has an albumin content of the order of 2%) is worked-up in conventional manner, which essentially means desalting (e.g. by gel or membrane filtration), concentration to the desired concentration, e.g. a 5, 20 or 25% solution, sterile filtration, and heat treatment against possibly remaining hepatitis virus. These working-up steps are commonly known (see e.g. Porath, J. et al., Nature 183 (1959), 1657 and British Pharmacopaeia (1973), P. 60) and do not form any particularly characterizing features of the new method according to the invention, the main feature of which resides in the combination of the above indicated two-step separation on anion and cation exchangers, applied on the particular starting material defined above.

In the different chromatographic separation operations in the method according to the invention any aqueous buffer system can be used, which gives the desired ph and the desired ionic strength and which is inert to the protein components present, in particular to the albumin. The same buffer system is preferably used both for the separation on the anion exchanger and on the cation exchanger. The preferred buffer systems are acetate buffers citrate buffers, and the like.

The choice of the anion and cation exchanger is not critical, but any type of ion exchanger, which does not act denaturating on the albumin, may, as a principle, be used. A great number of such ion exchangers are previously known and commercially available. Such ion exchangers are built up of a matrix of a hydrophilic organic polymer, which is insoluble but capable of swelling in water and which contains chemically bonded ion exchange groups. The matrix is preferably a polysaccharide based polymer such as cross-linked dextran, agarose, cross-linked agarose, cellulose and cross-linked cellulose.

The choice of the specific ion exchange groups of the matrix is not either very critical, but all types of known ion exchange groups may, as a principle, be used. The anion exchange groups may, for example, consist of aromatic or aliphatic amino groups, preferably dialkyl-aminoalkyl groups such as diethylaminoethyl, or quaternary aminoalkyl groups such as triethanolamino- or diethyl-(2hydroxypropyl)-aminoethyl. The cation exchange groups may, for example, be sulphonate, sulphate, phosphono, carboxyl or phenolic hydroxy groups, preferably carboxymethyl groups or sulphoalkyl groups such as sulphoethyl and sulphopropyl. (The above mentioned alkyl groups contain up to six carbon atoms, especially 1 – 4 carbon atoms.) The ion exchange groups may be bonded to the matrix by means of, for example, ether, ester or glyceryl bonds. The preparation of the gel-forming matrixes and the substitution thereof with ion exchange groups are techniques well known to the person skilled in the art; see e.g. U.S. Pat. No. 3,275,576, 3,277,025 and 3,629,230, British Pat. No. 1013585 and E.A. Peterson, "Cellulosic ion exchangers", North Holland Publishing Co. Amsterdam, London, 1970.

Particularly suitable anion exchangers are DEAE-Sephadex ® and DEAE-Sepharose ®, available from Pharmacia Fine Chemicals, Uppsala, Sweden, which consist of diethylaminoethyl-substituted cross-linked dextran and do. agarose respectively, SP-Sephadex ®, a sulphopropyl-substituted cross-linked dextran from the same company, is a particularly suitable cation exchanger, as is also sulphopropyl-substituted cross-linked agarose.

The capacity of the ion exchangers used in the method according to the invention may vary within fairly broad limits. The anion exchangers have an ion exchange capacity of 0.1 – 4.0 meq/g (dry weight), whereas the capacity of the cation exchangers amounts to 0.2 – 5.0 meq/g (dry weight).

According to a preferred embodiment of the method according to the invention an anion exchanger of the type cross-linked, especially DEAE-substituted agarose is used and the albumin is eluted out with an aqueous buffer of pH 4.7 – 4.9 and an ionic strength of 0.025 – 0.05, preferably after washing with a buffer of pH 5.0 – 5.2 and an ionic strength of 0.025 – 0.05. According to another preferred embodiment an anion exchanger of the type cross-linked, especially DEAE-substituted dextran is used and the albumin is eluted out with an aqueous buffer of pH 4.5 – 4.7 and an ionic strength of 0.05 – 0.1, preferably after washing with a buffer of pH 5.0 – 5.5 and an ionic strength of 0.05 – 0.1.

The invention is further illustrated in the following non-limiting examples, which refer to some specific embodiments of the albumin isolation method according to the invention.

EXAMPLE 1

(a) Separation of Factors I and VIII 400 ml of human blood were collected in 60 ml ACD solution (22.0 g tri-sodium citrate, 8.0 g citric acid, and 24.5 g dextrose per litre solution). After centrifugation for 30 minutes at 1350 g and +4° C the plasma was separated from the cell suspension. The plasma was frozen to −30° C and thawed at +4° C. The cryoprecipitate, containing fibrinogen (Factor I) and Factor VIII, was removed by centrifugation for 30 minutes at 1350 g and +4° C.

(b) Separation of Factors II, VII, IX and X 0.15 g (dry weight) DEAE-Sephadex ® A-50 (DEAE-substituted cross-linked dextran from Pharmacia Fine Chemicals, Uppsala, Sweden) was allowed to swell in 0.075M NaCl solution and was decanted 3 times. The swollen ion exchanger was autoclaved at 121° C for 0.5 hours, washed with 1M NaCl and suspended in 0.075M NaCl, and added to 100 ml of the supernatant from step a). The suspension was stirred for 45 minutes and then the DEAE-Sephadex ® A-50 gel with the adsorbed Factors II, VII, IX and X was filtered off, whereas the filtrate was frozen and stored at -20° C.

(c) Separation of IgG

The frozen plasma fraction from step b) was thawed at +4° C. and the pH was adjusted to pH 8.0 with 0.5M NaOH solution. 12.0 g polyethylene glycol 4000 (MW 3000 – 3700) was added to 100 ml of the pH adjusted plasma fraction. After stirring for 30 minutes at +4° C, the gamma G globulin containing precipitate was removed by centrifugation at 1800 g for 10 minutes at +4° C. The supernatant was adjusted to pH 4.8 with 0.5M HCl at +4° C, and then an additional amount of polyethylene glycol 4000 was added until a final concentration of 22% (w/v) was reached. The mixture was stirred at +4° C for 30 minutes and the albumin containing precipitate was collected by centrifugation at 1800 g for 10 minutes at +4° C. The precipitate was dissolved at +4° C in distilled water and pH was adjusted to 7.0 with 0.5M NaOh. The solution obtained (solution $P_2$) contained 75 mg albumin per ml.

(d) Purification on anion exchanger 1.5 g DEAE-Sephadex ® A-50 was swelled in 1M sodium acetate solution and transferred to 0.05M sodium acetate — acetic acid buffer, pH 5.2 and ionic strength (I) = 0.05 and packed into a column of 26 mm diameter giving a bed height of 87 mm and a total volume, $V_t$, of 46 ml. The column was washed with 2 × $V_t$ sodium acetate buffer pH 5.2, I = 0.05. 20 ml of the solution $P_2$ obtainedfrom step c) (containing 75 mg albumin/ml) was then applied to the column, which was then washed with 100 ml sodium acetate buffer pH 5.2, I = 0.05. The column was then eluted with a sodium acetate — acetic acid buffer, pH 4.7, I = 0.1, with an elution rate of 100 ml/h, equivalent to 19 cm/h. The albumin containing fraction (fraction DE2) — 50 ml — was collected.

pH was adjusted to 5.2 with 0.5M NaOH and the conductivity adjusted by dilution with distilled water to the original value of the DE2 fraction.

The DEAE-Sephadex ® column was regenerated by washing with sodium acetate — acetic acid buffer pH 4.0, I = 0.15 to elute residual protein material, and then with starting buffer, sodium acetate — acetic acid pH 5.2, I = 0.05.

(e) Purification on cation exchanger 1.5 g SP-Sephadex ® C-50 (sulphopropyl-substituted cross-linked dextran gel from Pharmacia Fine Chemicals, Uppsala, Sweden) was allowed to swell in 0.1M sodium acetate — acetic acid buffer pH 5.2, I = 0.1 and was packed into a 26 mm diameter column to a height of 70 mm and a total volume, $V_t$, of 37 ml. The column was washed with 2 × $V_t$ of the swelling buffer. 50 ml of the DE2 fraction fron step (d) (pH 5.2, I = 0.1) was applied to the column. The albumin containing fraction was eluted immediately with the same buffer (pH 5.2, I = 0.1) at an elution rate of 100 ml/h, equivalent to 19 cm/h, and 85 ml were collected. The column was regenerated by washing with sodium acetate — acetic acid buffer pH 8.0, I = 0.4 to elute remaining protein, and then with starting buffer, sodium acetate — acetic acid buffer, pH 5.2, I = 0.1.

(f) Working-up 110 g Sephadex ® G-25 Fine (cross-linked dextran gel from Pharmacia Fine Chemicals, Uppsala, Sweden) was allowed to swell in distilled water and packed into a column of 50 mm diameter giving a bed height of 25 cm and a total volume of 495 ml. 50 ml of the purified albumin containing fraction from step (e) were applied to the column and eluted with distilled water at a rate of 495 ml/h, equivalent to 25 cm/h. The salt-free albumin was collected — 95 ml — and lyophilized.

The lyophilized albumin was dissolved to a concentration of 20% (w/v) in physiological saline, containing 0.004M sodium caprylate, and pH was adjusted to 6.8 with sodium bicarbonate. The final product was obtained by sterile filteration through a 0.22 mµ filter and heat treatment at 60 ± 0.5° C for 10 hours. The purity and identity of the final product were checked by polyacrylamide gradient gel electrophoresis, crossed immunoelectrophoresis, immunodiffusion and gel filtration on Sephadex ® G-150 (cross-linked dextran gel from Pharamacia Fine Chemicals, Uppsala, Sweden), and the product was shown to contain more than 96% human plasma albumin with an albumin polymer concentration of less than 3.5%. The total yield was greater than 90% and the yield of albumin over the anion and cation exchange stages (d and e) was greater than 99%. Cl

EXAMPLE 2

120 ml sedimented suspension of DEAE-Sepharose ® (DEAE-substituted cross-linked agarose gen from Pharmacia Fine Chemicals, Uppsala, Sweden) was washed with 300 ml 1M sodium acetate, transferred to sodium acetate — acetic acid buffer pH 5.0, I = 0.025 and packed into a column of 50 mm diameter giving a bed height of 60 mm and a total volume ($V_t$) of 120 ml. The column was washed with 2 × $V_t$ sodium acetate buffer pH 5.0, I = 0.025 and 30 ml albumin solution from step c) in Example 1 were applied (solution $P_2$, 75 mg albumin/ml), and then the column was washed with starting buffer (pH 5.0, I = 0.025). The washing fractions were discarded. Then the albumin containing fraction was eluted (elution rate 25 cm/h) with sodium acetate buffer pH 4.9, I = 0.05 and 90 ml were collected.

The ionic strength of the solution obtained was increased to 0.1 and the pH adjusted to pH 5.2 by the addition of sodium acetate. This fraction was treated on an SP-Sephadex ® column and worked-up as in Example 1, steps e) and f) respectively. The final product was as pure and obtained in the same high yield as in Example 1.

The DEAE-Sepharose ® column was regenerated by washing with sodium acetate — acetic acid buffer pH 4.0, I = 0.05 to elute out remaining protein, and then with 2 × $V_t$ sodium acetate acetic acid buffer, pH 5.0, I = 0.025.

EXAMPLE 3

1.0 g CM-Sephadex ® C-50 ( carboxymethyl-substituted cross-linked dextran gel from Pharmacia Fine Chemicals, Uppsala, Sweden) was allowed to swell in sodium acetate — acetic acid buffer pH 6.2, i = 0.1 and was packed into a column of 16 mm diameter to a bed height of 17.5 cm giving a total volume ($V_t$) of 35 ml. The column was washed with 2 × $V_t$ starting buffer, pH 6.2, I = 0.1. 20 ml albumin containing solution from step (c) in Example 1 (solution $P_2$, 75 mg albumin/ml) were applied to the column. The albumin containing fraction was eluted ( elution rate 19 cm/h) with the same buffer, pH 6.2, I = 0.1, and 32 ml were collected.

The pH of this fraction was reduced — without changing the ionic strength — to pH 4.7 by the addition of 1M acetic acid, and the fraction was further purified on DEAE-Sephadex ® in analogy with step (d) in Example 1 (elution at pH 4.7, I = 0.1) and was worked-up as in step (f) in Example 1. The final product was as pure and obtained in the same high yield as in Example 1.

What we claim is:

1. A method of isolating albumin from plasma products, wherein a plasma fraction containing albumin in a dissolved form and being essentially free from the coagulation factors I, II, VII, VIII, IX and X and also from the main part of IgG, is subjected to a two-step chromatographic separation in arbitrary sequence (a) on an anion exchanger by means of an aqueous buffer of pH 4.5 – 4.9 and an ionic strength of 0.025 – 0.1, and (b) on a cation exchanger by means of an aqueous buffer of pH 5.2 – 6.5 and an ionic strength of 0.1 – 0.05, the albumin rich fractions from the first chromatographic separation step being collected and subjected to the second chromatographic separation step, and the albumin rich fraction from the second chromatographic separation step being collected, desalted and worked-up, and wherein said ion exchangers consist of matrixes of hydrophilic organic polymers, which are water-insoluble but water-swellable and which are substituted with ion exchange groups.

2. A method according to claim 1, wherein said chromatographic separations are carried out by column chromatography.

3. A method according to claim 1, wherein the buffer used for the separation on the cation exchanger has a pH of 5.2 – 5.7.

4. A method according to claim 1, wherein the first separation step is carried out on the anion exchanger and the second separation step on the cation exchanger, and wherein said first separation step comprises an introductory washing with an aqueous buffer of pH 5 – 5.5 and an ionic strength of 0.025 – 0.1 before the albumin is eluted out with a buffer of pH 4.5 – 4.9 and an ionic strength of 0.025 – 0.1.

5. A method according to claim 1, wherein the aqueous buffers used in said separation steps are selected from the group consisting of acetate buffers and citrate buffers.

* * * * *